(12) United States Patent
Porter

(10) Patent No.: US 8,480,619 B2
(45) Date of Patent: Jul. 9, 2013

(54) BALLOON CATHETER

(75) Inventor: Stephen C. Porter, Oakland, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/436,378

(22) Filed: Mar. 30, 2012

(65) Prior Publication Data

US 2012/0265135 A1 Oct. 18, 2012

Related U.S. Application Data

(60) Provisional application No. 61/474,461, filed on Apr. 12, 2011.

(51) Int. Cl.
*A61M 29/00* (2006.01)

(52) U.S. Cl.
USPC ............ 604/101.02; 604/96.01; 604/99.02; 604/102.02

(58) Field of Classification Search
CPC ...................................... A61M 29/00
USPC ........ 604/96.01, 99.02, 99.03, 99.04, 101.02, 604/102.02, 103.05, 164.13
See application file for complete search history.

(56) References Cited

U.S. PATENT DOCUMENTS

| | | | | |
|---|---|---|---|---|
| 4,813,934 A | * | 3/1989 | Engelson et al. | 604/99.02 |
| 5,035,705 A | * | 7/1991 | Burns | 606/194 |
| 5,209,728 A | | 5/1993 | Kraus et al. | |
| 5,360,403 A | * | 11/1994 | Mische | 604/101.02 |
| 5,378,237 A | * | 1/1995 | Boussignac et al. | 604/103.01 |
| 5,919,162 A | * | 7/1999 | Burns | 604/99.01 |
| 6,540,719 B2 | * | 4/2003 | Bigus et al. | 604/96.01 |
| 2005/0197668 A1 | * | 9/2005 | Lim et al. | 606/194 |
| 2011/0152760 A1 | * | 6/2011 | Parker | 604/96.01 |

FOREIGN PATENT DOCUMENTS

| | | |
|---|---|---|
| WO | 00/62852 | 10/2000 |
| WO | 02/096264 | 12/2002 |

OTHER PUBLICATIONS

PCT International Search Report and Written Opinion for International Patent Application No. PCT/US2012/031631, Applicant Boston Scientific Scimed, Inc., Forms PCT/ISA/210, 220, and 237, mailed Jul. 10, 2012 (15 pages).
PCT Invitation to Pay Additional Fees for International Application No. PCT/US2012/031631, Applicant Boston Scientific Scimed, Inc., Form PCT/ISA/206 and Annex to Form PCT/ISA/206, mailed May 31, 2012 (6 pages).

\* cited by examiner

*Primary Examiner* — Nicholas Lucchesi
*Assistant Examiner* — Gerald Landry, II
(74) *Attorney, Agent, or Firm* — Vista IP Law Group LLP

(57) ABSTRACT

A balloon catheter includes a balloon support member having a hollow axial lumen and open distal end for allowing passage of a guidewire therethrough, a balloon disposed around the balloon support member, and an annular balloon seal disposed proximate to a distal end of the balloon catheter. The seal defines a central passageway for allowing passage therethrough of a guidewire extending out the distal end of the balloon support member, and is configured to form a substantially fluid tight seal around each of a plurality of guidewires having different outer diameters.

10 Claims, 7 Drawing Sheets

BALLOON CATHETER

RELATED APPLICATION DATA

The present application claims the benefit under 35 U.S.C. §119 to U.S. provisional patent application Ser. No. 61/474,461, filed Apr. 12, 2011. The foregoing application is hereby incorporated by reference into the present application in its entirety.

FIELD

The present disclosure relates generally to medical devices. More particularly, the present disclosure relates to balloon catheters.

BACKGROUND

The use of intravascular medical devices has become an effective method for treating many types of vascular disease. In general, a suitable intravascular device is inserted into the vascular system of the patient and navigated through the vasculature to a desired target site. Using this method, virtually any target site in the patient's vascular system may be accessed, including the coronary, cerebral, and peripheral vasculature.

Catheters are often utilized to place medical devices such as stents and embolic devices at a desired location within the body. A medical prosthesis, such as a stent for example, may be loaded onto a catheter in a configuration having a reduced diameter and then introduced into the lumen of a body vessel. Once delivered to a target location within the body, the stent may then be expanded to an enlarged configuration within the vessel to support and reinforce the vessel wall while maintaining the vessel in an open, unobstructed condition. The stent may be configured to be self-expanding, expanded by an internal radial force such as a balloon, or a combination of self-expanding and balloon expandable.

Balloon catheters are used in a number of endovascular applications including temporarily or permanently occluding blood flow either distal or proximal of a treatment site during neurological examinations, assisting in neurovascular embolic coiling of an aneurysm or arteriovenous malformations (AVM), and dilating narrowed blood vessels caused by vasospasm. Single lumen balloon catheters have a balloon disposed around a hollow balloon support member. The balloon is typically formed by an impermeable tube having its proximal end bonded (sealed) to the balloon support member and its distal end bonded (sealed) to the support member or to the catheter tip, with the support member forming a lumen through which a guidewire passes. A few inflation/deflation channels are either punched or laser drilled in the balloon support member to allow fluid communication between the catheter lumen, the balloon support member lumen, and the interior of the balloon. The inner diameter of the catheter lumen is narrowed at a location distal of the inflation/deflation channels so that a seal is formed by a guidewire passing through the lumen. In particular, the inner diameter of the sealing portion of the lumen is sized to form a close tolerance opening for passage of the guidewire while still allowing freedom of axial and radial motion of the guidewire. As such, these seals require the use of a specific guidewire with low outer diameter variability.

However, depending on the specific medical application, it may be desirable to use a variety of guidewires having different outer diameters with a same model balloon catheter. Further, manufacturing processes may result in high variability in guidewire outer diameters. There is a need for a balloon distal end seal configured to form a substantially fluid tight seal around a variety of guidewires having different outer diameters. An inadequate seal between the balloon distal end and the guidewire may lead to premature balloon deflation and may also result in blood entering the balloon. The entrance of blood into the balloon may further result in poor balloon visibility and clot formation around the inflation/deflation channels. Poor balloon visibility and inability to quickly deflate the balloon during a procedure could lead to vessel damage, tissue damage from prolonged anoxia, and other serious complications.

SUMMARY

In one embodiment of the disclosed inventions, a balloon catheter includes a balloon support member having a hollow axial lumen and open distal end for allowing passage of a guidewire therethrough, a balloon disposed around the balloon support member, and an annular balloon seal disposed proximate to a distal end of the balloon catheter. The seal defines a central passageway for allowing passage therethrough of a guidewire extending out the distal end of the balloon support member, and is configured to form a substantially fluid tight seal around each of a plurality of guidewires having different outer diameters. Optionally, the balloon has a proximal end sealed to the balloon support member. Electively, the balloon seal is attached to the distal end of the balloon. Also optionally, the balloon seal is a compression fit seal mounted around a distal end of the balloon support member.

Alternatively or additionally, the balloon seal includes a compressible core surrounded by an overlying capsule. Optionally, the compressible core is made from expanded polytetrafluoroethylene. In some embodiments of the disclosed inventions, the overlaying capsule is made from polyethylene. In other embodiments, the overlaying capsule is made from a thermoplastic material.

Still further additionally or alternatively, the balloon seal includes a flexible member attached to a backing member, wherein the flexible member and the backing member define an annular space there between. In some embodiments, the backing member is selected from the group consisting of the balloon, the balloon support member, and a balloon catheter distal tip. Optionally, the space separates a portion of the flexible member from a portion of the backing member. A proximal end of the backing member may be attached to distal end of the balloon. In some embodiments of the disclosed inventions, the space is a closed space. In other embodiments, the space has an open proximal end in fluid communication with an interior of the balloon. In still other embodiments of the disclosed inventions, a distal end of the flexible member is attached to the backing member. In some of these embodiments, a proximal end of the flexible member is attached to the backing member. Optionally, the balloon may define an interior in fluid contact with the annular space. The flexible member may be configured to expand when the balloon is inflated.

In another embodiment of the disclosed inventions, a balloon catheter includes a balloon support member having a hollow axial lumen and open distal end for allowing passage of a guidewire therethrough, a balloon disposed around the balloon support member, and a compliant annular balloon seal disposed proximate to a distal end of the balloon catheter, the seal including a compressible core and defining a central passageway for allowing passage therethrough of a distal end portion of a guidewire extending out the distal end opening of the balloon support member, where the balloon seal is configured to form a substantially fluid tight seal around each of a plurality of guidewires having different outer diameters. Optionally, the balloon seal is a compression fit seal. The balloon seal may be mounted around a distal end of the balloon support member.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. The relative scale of select elements may have been exaggerated for clarity. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

FIGS. 3A and 3B respectively show the same balloon catheter mounted on two different guidewires.

DETAILED DESCRIPTION OF THE ILLUSTRATED EMBODIMENTS

Figure 1:
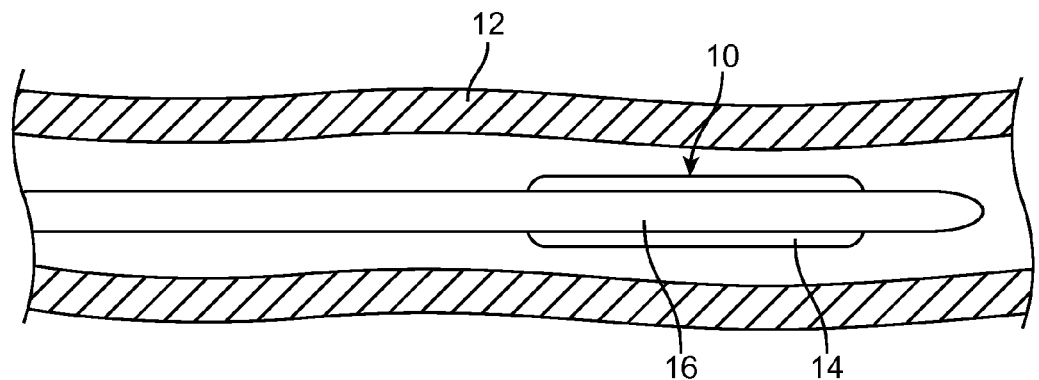
FIG. 1 is a plan view of a balloon catheter constructed according to one embodiment of the disclosed inventions, mounted on a guidewire, and disposed in a vessel.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 is a plan view of a balloon catheter 10 disposed in a blood vessel 12 and mounted on a guidewire 16. Balloon catheter 10 includes a balloon 14 configured to expand to seal vessels 12 within the anatomy of a patient. Balloon catheter 10 may be used for intravascular procedures. For example, balloon catheter 10 may be used in conjunction with other medical devices, such as a stent or a vaso-occlusive device, to treat and/or diagnose a medical condition.

Figure 2:
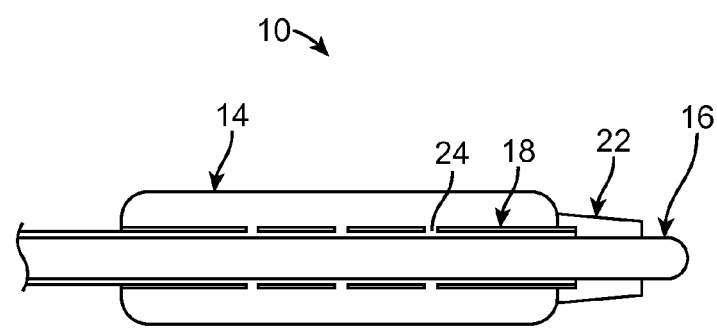
FIGS. 2 and 7 are schematic views of balloon catheters constructed according to two embodiments of the disclosed inventions and mounted on a guidewire.

FIG. 2 shows a balloon catheter 10 including a balloon support member 18, a balloon 14, and a distal balloon end seal 22. A wide variety of guidewires 16 may be used with the balloon catheter 10. Guidewires 16 facilitate navigation through the vasculature of a patient. Because the vasculature of a patient may be very tortuous, it is desirable to combine a number of performance features in a guidewire 16. For example, it is sometimes desirable that the guidewire 16 have a relatively high level of pushability and torqueability, particularly near its proximal end. It is also sometimes desirable that a guidewire 16 be relatively flexible, particularly near its distal end.

The guidewire 16 may have a solid cross-section or a hollow cross-section, and may be formed of any materials suitable for use, dependent upon the desired properties of the guidewire. Some examples of suitable materials include metals, metal alloys, and polymers. In some embodiments, it is desirable to use metals, or metal alloys that are suitable for metal joining techniques such as welding, soldering, brazing, crimping, friction fitting, adhesive bonding, etc.

The guidewire 16 may have a proximal portion formed of relatively stiff material such as straightened 304v stainless steel wire. Alternatively, proximal portion may be comprised of a metal or metal alloy such as a nickel-titanium alloy, nickel-chromium alloy, nickel-chromium-iron alloy, cobalt alloy, or other suitable material. In general, the material used to construct a proximal portion of a guidewire 16 may be selected to be relatively stiff for pushability and torqueability.

The guidewire 16 may have a distal portion formed of a relatively flexible material such as a straightened super elastic or linear elastic alloy (e.g., nickel-titanium) wire, or alternatively, a polymer material, such as a high performance polymer. Alternatively, distal portion may be comprised of a metal or metal alloy such as stainless steel, nickel-chromium alloy, nickel-chromium-iron alloy, cobalt alloy, or other suitable material. In general, the material used to construct distal portion may be selected to be relatively flexible for trackability. The distal portion may also be formed of a linear elastic nickel-titanium alloy, for example, linear elastic nitinol.

The balloon catheter 10 includes a balloon support member 18. In use, the balloon support member 18 is slidably disposed around a guidewire 16. The balloon support member 18 generally has a tubular shape with channels 24 formed therein. The channels 24 are formed in the balloon support member 18 using techniques such as punching and laser drilling. When supporting a balloon 14 in a balloon catheter 10, as shown in FIG. 2, at least a part of the balloon support member 18 is disposed inside the balloon 14. The balloon support member 18 defines a lumen 26 that accommodates a guidewire 16 and provides a fluid path for inflation and deflation of the balloon 14. The lumen 26 has open proximal and distal ends to allow passage of a guidewire therethrough. The balloon support member 18 also provides axial support to resist shortening via any pre-biased tension or lengthening of the balloon 14 during inflation.

The structure of the balloon support member 18 allows fluid communication between the lumen 26 the balloon 14 through the channels 24. An inflation source not shown is fluidly connected to the lumen 26 into which it can introduce and withdraw inflation fluid and/or contrast medium. From the proximal opening of the lumen 26, the introduced fluid travels around a guidewire 16 disposed in the lumen 26, through the channels 24, and into the interior of the balloon 14 to facilitate inflation and deflation thereof.

As shown in FIGS. 3A to 6, the balloon support member 18 can also be a slotted tube. In these embodiments, the balloon support member is generally a stack of annular segments 28 separated by slots 30 and connected by beams 32. Like the channels 24 in the embodiment depicted in FIG. 2, the slots 30 provide a fluid path for inflation and deflation of the balloon 14. Various embodiments of arrangements and configurations of slots 30 are contemplated. Slots 30 enhance the flexibility of balloon support member 18 while retaining suitable torque transmission characteristics. Slots 30 are formed such that the annular segments 28 are interconnected by one or more beams 32, i.e., the portion of balloon support member 18 remaining after slots 30 are formed therein. Such an interconnected structure displays a relatively high degree of torsional stiffness, while retaining a desired level of lateral flexibility.

Slots 30 can be arranged along the length of, or about the circumference of, balloon support member 18 to achieve desired properties. Other characteristics, such as slot size, slot shape and/or slot angle with respect to the longitudinal axis of balloon support member 18, can also be varied along the length of balloon support member 18 in order to vary the flexibility or other properties. In other embodiments, moreover, it is contemplated that the portions of the balloon support member 18 may not include any such slots 30.

Slots 30 can be formed by methods such as micro-machining, saw-cutting (e.g., using a diamond grit embedded semi-conductor dicing blade), electron discharge machining, grinding, milling, casting, molding, chemically etching or treating, laser cutting, or other known methods, and the like. In some such embodiments, the structure of the balloon support member 18 is formed by cutting and/or removing portions of the tube to form slots 30. Methods for manufacturing balloon catheter 10 may include forming slots 30 in balloon support member 18 using any of these or other manufacturing steps.

Balloon support member 18 and/or other components of balloon catheter 10 may be made from a metal, metal alloy, polymer (some examples of which are disclosed below), a metal-polymer composite, ceramics, combinations thereof, and the like, or any other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to above, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2-0.44% strain before plastically deforming.

In some embodiments, the linear elastic and/or non-super-elastic nickel-titanium alloy is an alloy that does not show any martensite/austenite phase changes that are detectable by DSC and DMTA analysis over a large temperature range. For example, in some embodiments, there may be no martensite/austenite phase changes detectable by DSC and DMTA analysis in the range of about −60° C. to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of balloon support member 18 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of balloon catheter 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of balloon catheter 10 to achieve the same result.

In some embodiments, a degree of MRI compatibility is imparted into balloon catheter 10. For example, to enhance compatibility with Magnetic Resonance Imaging (MRI) machines, it may be desirable to make balloon support member 18, or other portions of the balloon catheter 10, in a manner that would impart a degree of MRI compatibility. For example, balloon support member 18, or portions thereof, may be made of a material that does not substantially distort the image and create substantial artifacts (artifacts are gaps in the image). Certain ferromagnetic materials, for example, may not be suitable because they may create artifacts in an MRI image. Balloon support member 18, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The entire balloon catheter 10 can be made of the same material along its length, or in some embodiments, can include portions or sections made of different materials. In some embodiments, the material used to construct balloon catheter 10 is chosen to impart varying flexibility and stiffness characteristics to different portions of balloon catheter 10. For example, a proximal portion and a distal portion of balloon catheter 10 may be formed of different materials, for example materials having different moduli of elasticity, resulting in a difference in flexibility. In some embodiments, the material used to construct proximal portion can be relatively stiff for pushability and torqueability, and the material used to construct distal portion can be relatively flexible by comparison for better lateral trackability and steerability. For example, proximal portion can be formed of straightened 304v stainless steel wire or ribbon and distal portion can be formed of a straightened super elastic or linear elastic alloy, for example a nickel-titanium alloy wire or ribbon.

Referring to FIG. 2, the balloon 14 is positioned on the balloon support member 18 such that the balloon 14 overlies the portion of the balloon support member 18 having channels 24 formed therein. The balloon 14 may be made of a highly compliant material that elastically expands upon pressurization. Because the balloon 14 elastically expands from the deflated state to the inflated state, the balloon 14 has an extremely low profile in the deflated state may be used without folding the balloon 14. The balloon 14 is sealed at its proximal end to the balloon support member 18. When the balloon catheter 10 is mounted on a guidewire 16, a balloon distal end seal 22 at the distal end of the balloon 14 forms a substantially fluid tight seal about the guidewire 16. As explained in further detail below, the balloon distal end seal 22 is configured to form a substantially fluid tight seal around a variety of guidewires 16 having different outer diameters.

The balloon may be formed of silicone, urethane polymer, or an extruded thermoplastic polyisoprene rubber such as a 40 A, 25 A, 15 A and 5 A durometer hydrogenated polyisoprene rubber, which is commercially available under the trade name Chronoprene™ from Advancesource Biomaterials, Inc. Hydrogenated polyisoprene provides a balloon having superior performance and manufacturing attributes. In particular, hydrogenated polyisoprene may be processed with standard polyolefin processing equipment to obtain balloon tubing having a wall thickness of approximately 0.001 inches to 0.010 inches and a corresponding inside diameter of approximately 0.016 inches to 0.028 inches. Such tubing produces balloons having a nominal inflated outside diameter of approximately 3.0 mm to 7.5 mm. The highly compliant balloon preferably elastically expands at pressures less than 1.0 ATM. The highly compliant balloon may have a pressure compliance of 2.0 mm/ATM or more at pressures less than 2.0 ATM. The highly compliant balloon may have a volumetric compliance of approximately 0.3 mm per 0.01 ml to 0.5 mm per 0.01 ml at pressures less than 2.0 ATM, for balloons having a nominal diameter of approximately 3.5 mm and a length of approximately 10 mm to 15 mm. The ends of the balloon are attached to the balloon support member 18 and the flexible distal tip using conventional bonding means such as thermal bonding using a hot air source or a laser. The balloon support member 18, excluding the balloon 14 and distal flexible tip, can be coated with hydrophilic coatings such as Hydropass, Hydrolene or Bioslide.

Figure 3A:
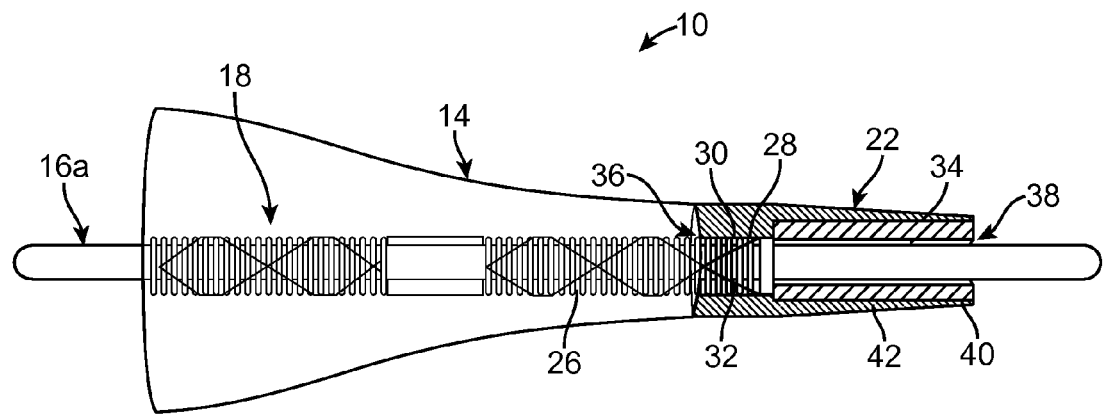
FIGS. 3A and 3B are detailed perspective views of the distal end of a balloon catheter constructed according to one embodiment of the disclosed inventions, with the balloon shown in shadow and part of the balloon distal end seal cut away for clarity.
Figure 3B:
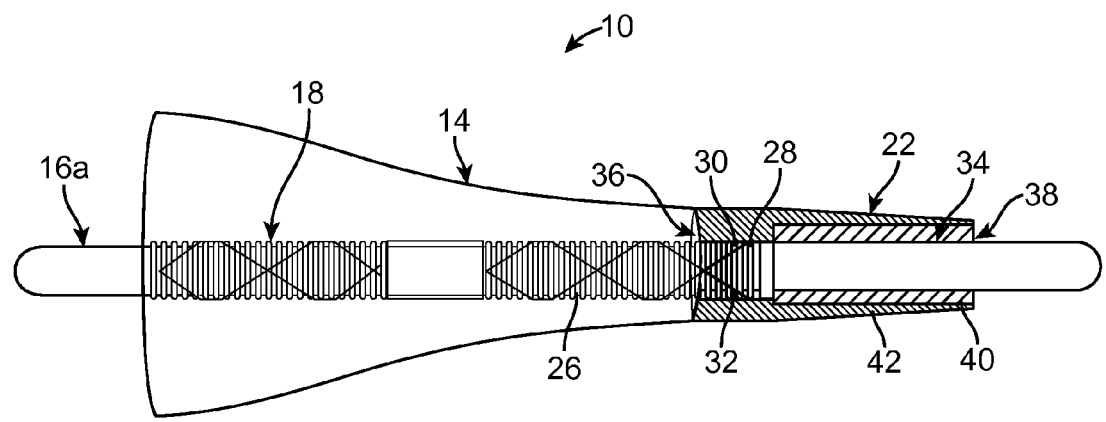

In the embodiments in FIGS. 3A and 3B, the balloon distal end seal 22 is a generally tubular structure defining a central passageway 34 with proximal and distal openings 36, 38. The central passageway 34 allows passage therethrough of a guidewire 16 extending out the distal end of the balloon support member 18. As shown in FIG. 2, the proximal end of the balloon distal end seal 22 is sealed to the distal end of the balloon 14, forming a annular fluid tight seal. As a result, distal flow of fluid from the balloon 14 is limited to through the proximal opening 36 and into the central passageway 34 of the balloon distal end seal 22. When the balloon catheter 10 is mounted on a guidewire 16, the balloon distal end seal 22 forms a substantially fluid tight seal against the guidewire 16, thereby limiting distal flow of fluid from the balloon 14.

The balloon distal end seal 22 includes a tubular core liner 40 disposed inside of a tubular capsule 42. The core liner 40 forms the central passageway 34 of the balloon distal end seal 22. The core liner 40 may be made from expanded polytetrafluoroethylene ("ePTFE"). ePTFE is easily compressible so that the core liner 40 may be radially compressed to enlarge the distal opening 38 and allow passage of guidewires 16 with larger outer diameters. For example, in FIGS. 3A and 3B, the same balloon catheter 10 is respectively mounted on guidewires 16a, 16b with outer diameters of 0.012 inches (FIG. 3A) and 0.0145 inches (FIG. 3B), respectively. Natural expansion of the core liner 40 against a guidewire 16 disposed in the central passageway 34 of the balloon distal end seal 22 forms a compression fit seal that is substantially fluid tight. PTFE also possesses a low coefficient of friction. Accordingly, friction between a guidewire 16 and the central passageway 34 is minimized to facilitate guidewire movement relative to the balloon catheter 10. Materials from which the core liner 40 may be made include, but are not limited to, elastomeric and/or porous polymers, hydrogel polymers, or other materials which may expand or contract when a force acts upon them.

The capsule 42 may be made from any flowable support material, such as high density polyethylene or polyether block amide (PEBAX®) or the material from which the balloon 14 is made. The capsule 42 may be laminated onto the core liner 40. In such a case, the lamination may be performed with the core liner 40 mounted on a mandrel having a larger outer diameter than the unstressed core liner 40 inner diameter to ensure the core liner 40 maintains compressibility over a range of central passageway 34 sizes. In some embodiments, the balloon support member 18 functions as the capsule 42 around the core liner 40.

The radial thicknesses of the core liner 40 and the capsule 42 can be modified to configure the balloon catheter 10 for use with a range of guidewire 16 outer diameters. Further, the expansibility, porosity (intermodal size), and inner diameter of the core liner 40 can also be modified to further configure the balloon distal end seal 22. Moreover, the capsule 42 may be modified to affect the natural and maximal expanded diameter of the distal opening 38.

Figure 4:
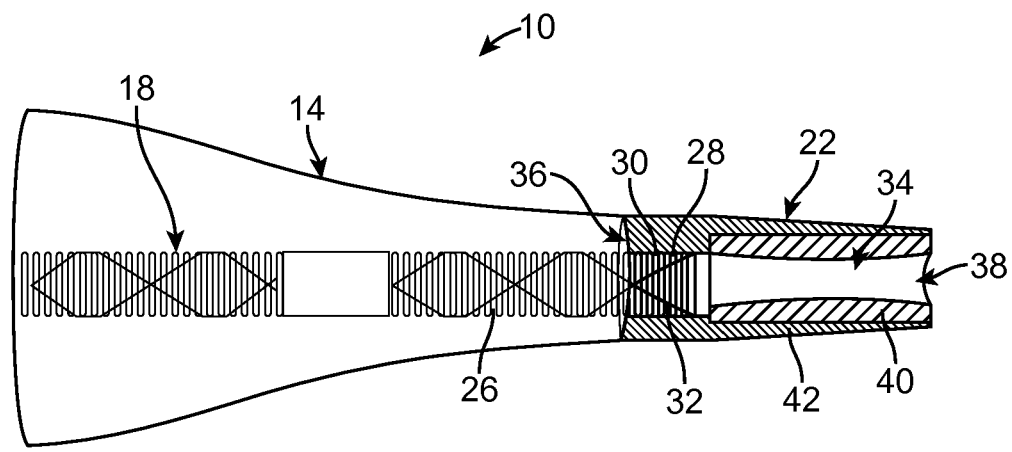
FIGS. 4 to 6 are detailed perspective views of the distal end of balloon catheters constructed according to various embodiments of the disclosed inventions, with the balloon shown in shadow and part of the balloon distal end seal cut away for clarity.

FIG. 4 shows the balloon distal end seal 22 of a balloon catheter 10 not mounted on a guidewire 16. Without a guidewire 16 to restrain the core liner 40, the core liner 40 expands partially into the lumen. In the embodiment in FIGS. 3A, 3B, and 4, the core liner 40 is positioned next to the balloon support member 18 such that the distal end of the balloon support member 18 in roughly the same axial position as the proximal end of the core liner 40. The capsule 42 overlies both the distal end of the balloon support member 18 and the core liner 40.

Figure 5:
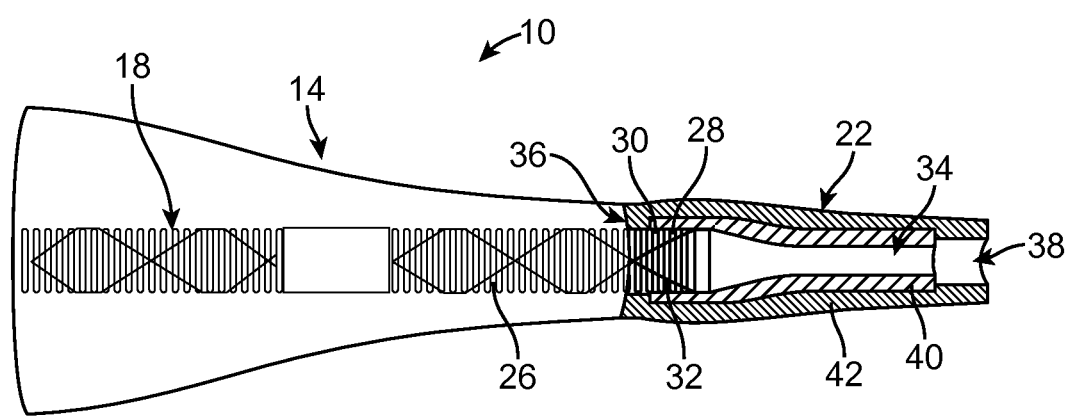

In the embodiment in FIG. 5, the proximal end of the core liner 40 overlies the distal end of the balloon support member 18, providing an additional compression fit.

Figure 6:
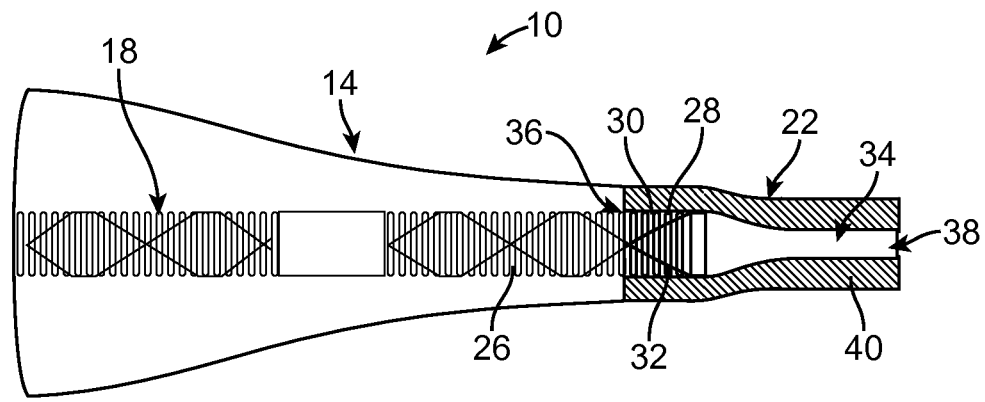
Figure 7:
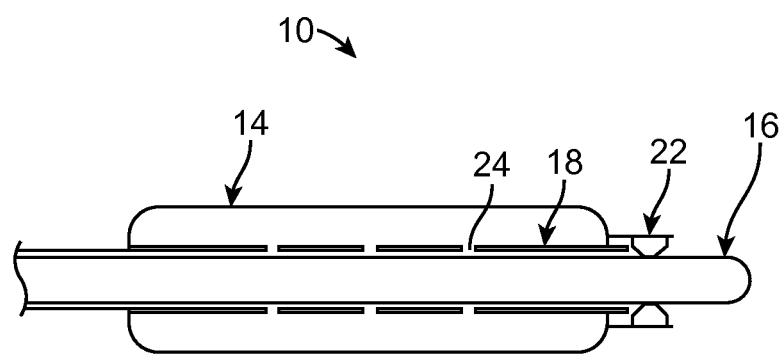

In the embodiment in FIG. 6, the balloon distal end seal 22 is a bare core liner 40 without an overlying capsule 42. The proximal end of the core liner 40 overlies the distal end of the balloon support member 18. The core liner 40 in FIG. 6 may be made of an elastomeric material with different properties than the core liners 40 in the embodiments depicted in FIGS. 3, 4, and 5, in that the material can stretch in the radial direction while achieving the same sealing effect.

FIGS. 7 to 10 show embodiments of the inventions wherein the balloon distal end seal 22 includes flexible annular seal 48 that extends distally from the distal end of the balloon 14. As shown in greater detail in FIGS. 8 and 9, flexible annular seal 48 can be disposed inside of a distal end of the balloon 14. In other similar embodiments, the annular seal 48 may also be disposed inside of a separate balloon catheter distal tip. The annular seal 48 is generally cylindrical in shape and formed of a flexible material. The annular seal 48 is softer than the balloon 14. An intermediate portion 50 of the annular seal 48 is biased radially inward toward the longitudinal axis of the cylinder, creating an annular space 52 that separates a portion of the annular seal 48 from a portion of the balloon 14. When the balloon catheter 10 is mounted on a guidewire 16, the inward bias of the intermediate portion 50 urges the annular seal 48 against the guidewire 16 central passageway 34, and forms a compression fit seal that is substantially fluid tight.

The annular seal 48 has a proximal end 54 and a distal end 56 on either side of the middle portion of the intermediate portion 50 and the space 52. In the embodiment in FIG. 8, both the proximal and distal ends 54, 56 are fluidly sealed to the balloon 14, thereby closing the space 52. The material and dimensions of the balloon 14 and the annular seal 48 can be modified to configure the balloon catheter 10 for use with a range of guidewire 16 outer diameters. Further, the space 52 can be filled with materials having varying degrees of compressibility to further configure the balloon distal end seal 22.

Figure 9:
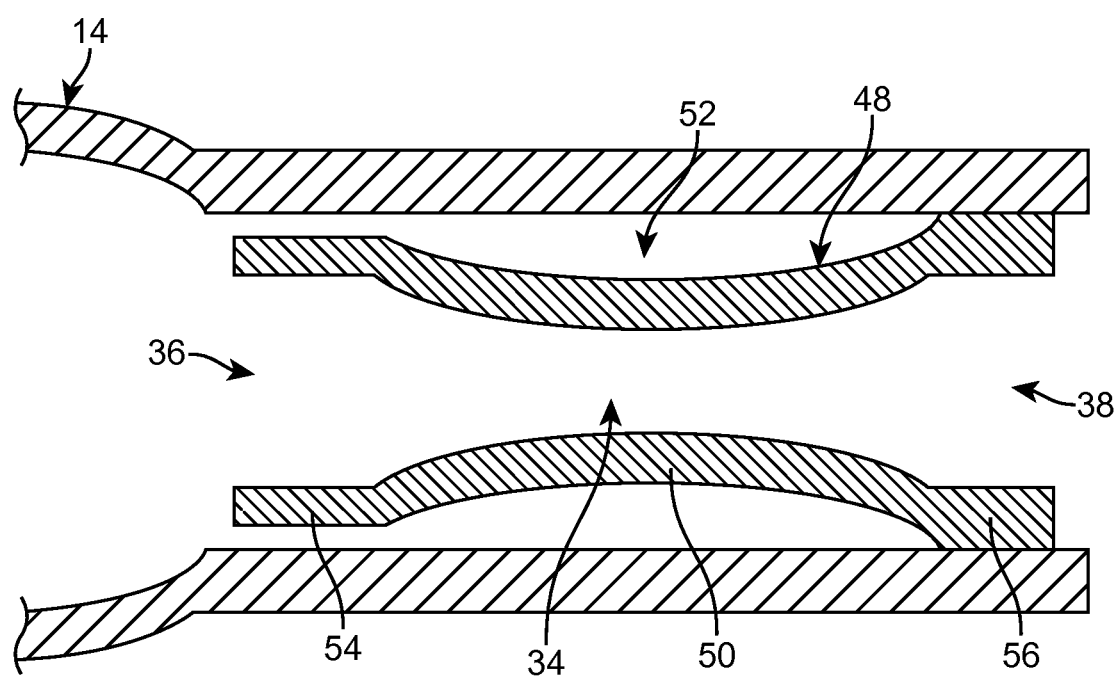
FIG. 9 is a detailed longitudinal cross-sectional view of the distal end of balloon catheters constructed according to another embodiment of the disclosed inventions.

In the embodiment in FIG. 9, only the distal end 56 is fluidly sealed to the balloon 14. The proximal end 54 of the annular seal 48 is unattached, allowing fluid communication between the space 52 and the interior of the balloon 14. During inflation with the balloon catheter 10 is mounted on a guidewire 16, the increased pressure from the inflation fluid in the balloon 14 is transmitted to the space 52 behind the annular seal 48, decreasing the size of the distal opening 38, and sealing the balloon distal end seal 22 against the guidewire 16. At other times, the size of the distal opening 38 is increased with the annular seal 48 in a relaxed state to allow axial movement of a guidewire 16.

Figure 10:
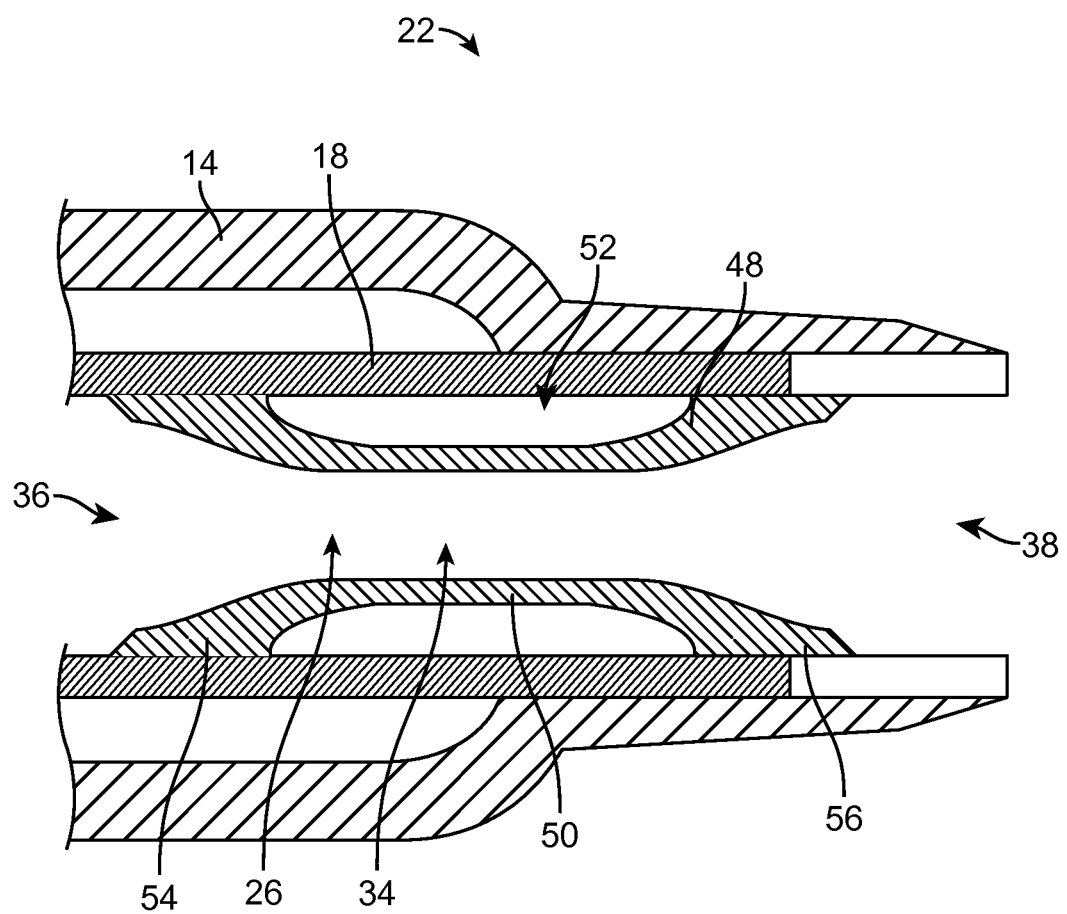
FIG. 10 is a detailed longitudinal cross-sectional view of the distal end of balloon catheters constructed according to yet another embodiment of the disclosed inventions.

In the embodiment in FIG. 10, the balloon distal end seal 22 is located partially within a distal section of the balloon support member lumen 26. In this embodiment, the proximal end 54 of the annular seal 48 is fluidly sealed to the balloon support member 18. The distal end 56 of the annular seal 48 is fluidly sealed to the balloon support member 18 and the balloon 14. In some embodiments, channels 24 in the balloon support member 18 allow fluid communication between the space 52 and the interior of the balloon 14. In other embodiments, the balloon support member 18 functions as a capsule 42 around a core liner 40.

Figure 8:
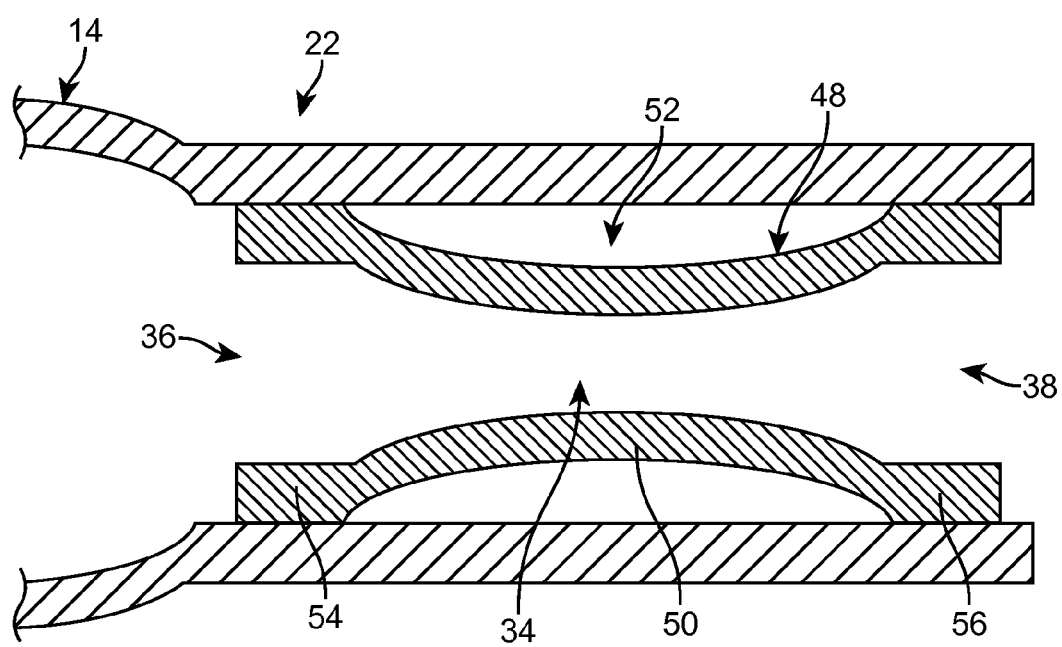
FIG. 8 is a detailed longitudinal cross-sectional view of the distal end of balloon catheters constructed according to one embodiment of the disclosed inventions.

In the embodiments in FIGS. 8 to 10, the annular seal 48 is disposed inside of and at least partially attached to various backing members, i.e., the balloon 14, the balloon support member 18, and the catheter distal tip. In other embodiments, other parts of the balloon catheter 10 may form the backing member, as long as these parts provide a lumen in which the annular seal 48 may be disposed. As shown in FIG. 10, the annular seal 48 may be attached to more than one backing member, e.g., the balloon 14 and the balloon support member 18.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A balloon catheter, comprising:
   a balloon support member having a hollow axial lumen and open distal end for allowing passage of a guidewire therethrough;

a balloon disposed around the balloon support member; and an annular balloon seal disposed proximate to a distal end of the balloon catheter, the balloon seal comprising a flexible member having a distal end attached to and forming a fluid-tight seal with a distal end of the balloon, the flexible member and an interior wall of the balloon defining an annular space, wherein an open gap between a proximal end of the flexible member and the interior balloon wall allows for fluid communication between an interior of the balloon and the annular space, and wherein the balloon seal defines a central passageway for allowing passage therethrough of a guidewire extending out the distal end of the balloon support member, wherein the balloon seal is configured to form a substantially fluid tight seal around each of a plurality of guidewires having different outer diameters.

2. The balloon catheter of claim 1, wherein the balloon is attached to the balloon support member.

3. The balloon catheter of claim 1, wherein the balloon seal is a compression fit seal.

4. The balloon catheter of claim 1, wherein the flexible member is configured to expand when the balloon is inflated.

5. A balloon catheter, comprising:
a balloon support member having a hollow axial lumen and open distal end for allowing passage of a guidewire therethrough;
a balloon disposed around the balloon support member; and
a balloon seal disposed proximate to a distal end of the balloon catheter, the balloon seal comprising a compliant annular member having a distal end attached to and forming a fluid-tight seal with a distal end of the balloon, the compliant annular member and an interior wall of the balloon defining an annular space, wherein an open gap between a proximal end of the compliant annular member and the interior balloon wall allows for fluid communication between an interior of the balloon and the annular space, and wherein the balloon seal defines a central passageway for allowing passage therethrough of a guidewire extending out the distal end of the balloon support member, wherein the balloon seal is configured to form a substantially fluid tight seal around each of a plurality of guidewires having different outer diameters.

6. The balloon catheter of claim 5, wherein the balloon seal is a compression fit seal.

7. The balloon catheter of claim 5, wherein the balloon is attached to the balloon support member.

8. The balloon catheter of claim 5, wherein the compliant annular member is configured to expand when the balloon is inflated.

9. The balloon catheter of claim 5, wherein the compliant annular member is configured to contract the central passageway when the balloon is inflated.

10. The balloon catheter of claim 1, wherein the flexible member is configured to contract the central passageway when the balloon is inflated.

* * * * *